United States Patent [19]

Williamson

[11] 4,335,710

[45] Jun. 22, 1982

[54] DEVICE FOR THE INDUCTION OF SPECIFIC BRAIN WAVE PATTERNS

[75] Inventor: John D. Williamson, North Canton, Ohio

[73] Assignee: Omnitronics Research Corporation, Akron, Ohio

[21] Appl. No.: 112,537

[22] Filed: Jan. 16, 1980

[51] Int. Cl.³ .............................................. A61N 1/34
[52] U.S. Cl. .................................................. 128/1 C
[58] Field of Search ............................... 128/1 C, 1 R

[56] References Cited

U.S. PATENT DOCUMENTS

| | | | |
|---|---|---|---|
| 2,466,054 | 4/1949 | Siebel | 128/1 R |
| 3,160,159 | 12/1964 | Hoody et al. | 128/1C |
| 3,576,185 | 4/1971 | Schulz et al. | 128/1 C |
| 3,712,292 | 1/1973 | Zentmeyer, Jr. | 128/1 C |
| 3,753,433 | 8/1973 | Bakerich et al. | 128/1 C |
| 3,884,218 | 5/1975 | Monroe | 128/1 C |
| 3,892,957 | 1/1975 | Freeman | 128/732 |
| 4,034,741 | 7/1977 | Adams et al. | 128/1 C |

FOREIGN PATENT DOCUMENTS 1165541 10/1969 United Kingdom ............... 128/1 C

*Primary Examiner*—William E. Kamm
*Attorney, Agent, or Firm*—Hamilton, Renner & Kenner

[57] ABSTRACT

Brain wave patterns associated with relaxed and meditative states in a subject are gradually induced without deleterious chemical or neurological side effects. A white noise generator (11) has the spectral noise density of its output signal modulated in a manner similar to the brain wave patterns by a switching transistor (18) within a spectrum modulator (12). The modulated white noise signal is amplified by output amplifier (13) and converted to an audio signal by acoustic transducer (14). Ramp generator (16) gradually increases the voltage received by and resultant output frequency of voltage controlled oscillator (17) whereby switching transistor (18) periodically shunts the high frequency components of the white noise signal to ground.

11 Claims, 2 Drawing Figures

DEVICE FOR THE INDUCTION OF SPECIFIC BRAIN WAVE PATTERNS

TECHNICAL FIELD

The present invention relates generally to a device for effecting deep relaxation in a subject. More particular, the present invention relates to a device for the induction of brain wave patterns associated with relaxed and meditative states in a human subject, commonly known as a "brain driver".

BACKGROUND ART

It has long been recognized that most mammals and in particular humans exhibit distinct recurring electrical frequencies in their brain wave patterns, each of which is related to separately identifiable physiological states. Brain waves having dominant frequencies from approximately 8–13 Hz, inclusive, are known as Alpha frequency brain waves and are associated with relaxed and meditative states as would occur when a subject has his eyes closed but is conscious and not thinking.

Techniques and devices which attempt to promote natural relaxation may be generally classified as passive or active. Passive devices serve merely to mask out irritating external noises with more pleasant sounds or utilize random or "white noise" to psychologically distract the subject from events which inhibit natural relaxation. Active devices seek to intentionally induce Alpha frequency brain waves in the subject, a phenomena known as "brain driving". Irrespective of the manner in which such brain waves are induced, a subject whose brain waves are principally in the Alpha frequency range will become deeply relaxed and exhibit the same beneficial reduced muscular tension and lowered anxiety and adrenalin levels as are associated with a naturally occurring state of relaxation.

Typical of the numerous passive devices are those which vary the output signal from a "white noise" source and convert the same to an accoustical signal, resulting in pleasant masking sounds. In one device, the white noise source output has its amplitude varied by a saw tooth wave form to produce sounds similar to waves repeatedly breaking in a surf. In another device, the output signal from a "white noise" source has its spectral content and amplitude varied in direct response to a subject's instantaneous dominant brain wave frequency and amplitude, respectively, producing a feedback signal to be utilized by the subject to recognize his present physiological state. All passive devices suffer from a fundamental inadequacy in that they cannot actually induce Alpha frequency brain waves with its associated relaxed and meditative condition.

Currently only three basic techniques for forcing a subject into a state exhibiting Alpha frequency brain waves are known to exist. Perhaps the most widely used is chemical tranquilizers, always subject to potentially grave known and unknown negative side effects or contraindications. The other techniques for "brain driving" involve the use of very bright, quickly flashing lights, direct electrical pulse stimulation of the brain through skin electrodes, or some combination thereof. In either instance, the lights or electrical pulses are synchronized to occur at a rate within the Alpha frequency range, i.e., from about 8 to 14 Hz. However, such flashing lights are not only irritating but may likely initiate a seizure in epileptic individuals. Electrical pulses are not only irritating, but also may produce unknown, deleterious side effects upon other parts of the brain or other neurological activity. Moreover, these devices attempt to very abruptly force the subject from an active and possibly highly emotional state to a highly relaxed and meditative state, thereby greatly increasing the likelihood of failure.

DISCLOSURE OF INVENTION

It is, therefore, an object of the invention to provide a device for the induction of brain wave patterns associated with relaxed and meditative states in a subject in a safe manner without deleterious or irritating side effects or contraindications.

It is a further object of the invention to provide a device for the induction of brain wave patterns associated with relaxed and meditative states in a subject, as above, which gradually induces such state in the subject.

It is yet a further object of the invention, to provide a device for the induction of brain wave patterns associated with relaxed and meditative states in a subject, as above, which utilizes a pleasing sound that is modulated and programmed in such manner as to induce Alpha frequency brain wave patterns only in those brain structures where it naturally occurs.

It is still a further object of the invention to provide a device for the induction of brain wave patterns associated with relaxed and meditative states in a subject, as above, which ultimately terminates all variations in modulation of the sound thereby freeing and encouraging the subject's brain to assume whatever somnolent brain wave patterns occur naturally to the subject.

It is still a further object of the invention to provide a device for the induction of brain wave patterns associated with relaxed and meditative states in a subject, as above, which includes a source of white noise and a circuit for modulating the spectral noise density of the white noise in a manner similar to the brain wave patterns associated with relaxed and meditative states so as to promote the gradual transition to an Alpha frequency brain wave condition and the continuous maintenance of the subject in that condition.

These and other objects and advantages of the present invention over existing prior art forms will become more apparent and fully understood from the following description in conjunction with the accompanying drawings.

In general, a device for the induction of brain wave patterns associated with relaxed and meditative states in a subject comprises a signal generator for generating a white noise signal having a uniform spectral noise density, a modulation circuit for receiving and modulating the white noise signal, and means for receiving the modulated noise signal and coupling it to the subject. The modulation circuit modulates the white noise signal in a manner similar to the brain wave patterns associated with relaxed and meditative states in the subject, thereby actively gradually inducing such state in the subject.

PREFERRED EMBODIMENT FOR CARRYING OUT THE INVENTION

Figure 1:
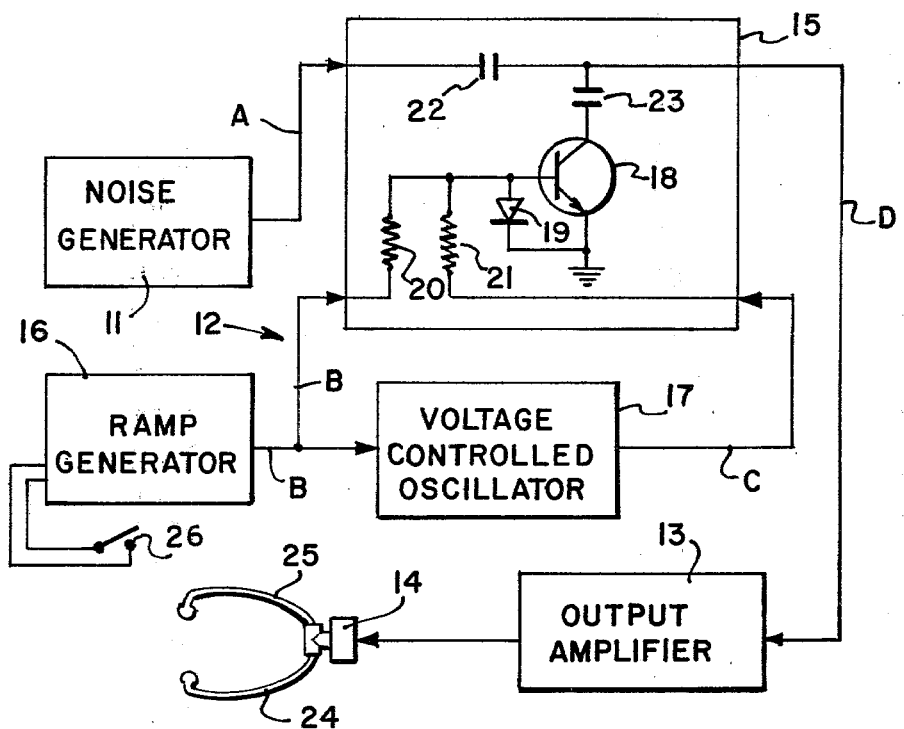
FIG. 1 is a block diagram of an exemplary device according to the concept of the present invention, and depicts the spectral-noise density modulator schematically.

FIG. 1 illustrates a device, generally indicated by the numeral 10, for the reduction of stress in an individual by the induction of brain wave patterns associated with relaxed and meditative states. Device 10 broadly includes white noise generator 11, spectrum modulator 12, output amplifier 13, and acoustic transducer 14.

White noise generator 11 may be any conventional noise generator, either of the random or impulsive type, that has a level frequency spectrum over the frequency range of interest. One generator found suitable for use herein included an operational amplifier providing a thermal noise signal and an amplification stage.

Spectrum modulator 12 includes transistor shunt gate 15, ramp generator 16, and voltage control oscillator (hereinafter referred to as VCO) 17. Transistor shunt gate 15 includes a conventional NPN switching transistor 18, a by-pass diode 19, two summing resistors 20 and 21, and two capacitors 22 and 23. Ramp generator 16 may be any conventional ramp generator such as an integrator having a period as detailed hereinbelow and having a maximum voltage compatible with VCO 17 and transistor shunt gate 15. A switch 26 may be provided for resetting ramp generator 15 to its zero point, which for an integrator may be its maximum voltage of negative polarity, referred to for convenient reference as $-V$.

VCO 17 may be any of the multitude of well-known astable multivibrators whose output frequency is a function of the voltage of its input signal. The frequency range of the output signal from VCO 17 should be slightly greater than the frequency range of alpha brain wave patterns and preferably should vary linearly from it highest output frequency when ramp generator 16 is at its maximum voltage of negative polarity ($-V$) to its lowest output frequency when ramp generator 16 is at its maximum voltage of positive polarity ($+V$). Where the Alpha brain wave frequency range is taken to be from approximately 8 to 13 Hz, inclusive, it is adequate to provide a VCO 17 output signal frequency range from approximately 5 to 14 Hz, inclusive.

Acoustic transducer 14 may be any conventional device for converting the electrical output signal from transistor shunt gate 15 to an audio signal. In order to increase the likelihood of relaxation in the subject, it is, however, highly desirable to provide the least intrusive coupling between the transducer and the subject while minimizing acoustical background distractions. Therefore, it has been found preferable to utilize a conventional headphone transducer having pneumatic tubes 24, 25 adopted to carry the audio signal to each ear of the subject without applying noticeable pressure to the subject's head.

The interconnection of the various elements described above is straightforward. The collector of switching transistor 18 is connected through capacitors 23 and 22, to noise generator 11 and, through capacitor 23 to output amplifier 13, so that both may receive the output signal from noise generator 11. The output signal from ramp generator 16 is received by both VCO 17 and, through resistor 20, the base of switching transistor 18. The output signal from VCO 17 is also received, through resistor 21, by the base of switching transistor 18. The anode of diode 19 is connected to the base of switching transistor 18, and has its cathode connected to ground along with the emitter of switching transistor 18. The output signal from output amplifier 13 is received by acoustic transducer 14.

Figure 2:
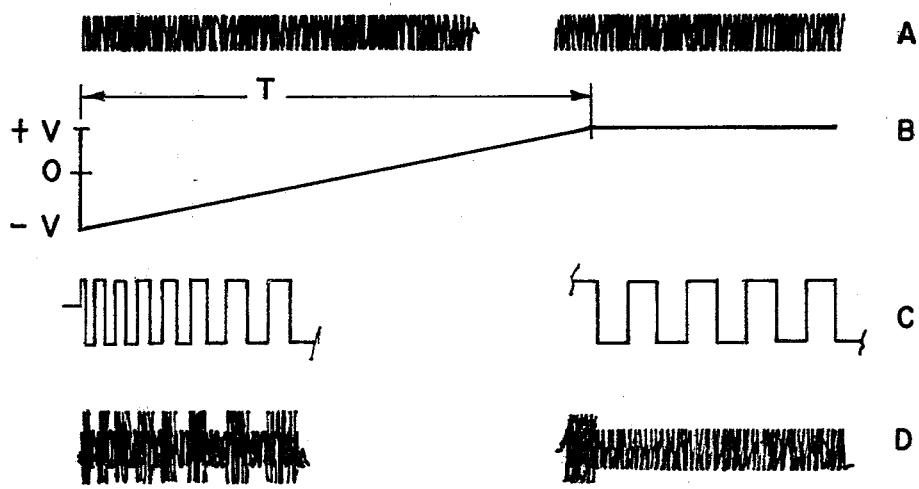
FIG. 2 is a somewhat schematic representation of the voltage waveforms at various points in the device shown in FIG. 1, and although the various waveforms are in approximate time coordination with each other, they are not necessarily to scale.

To better visualize the operation of device 10, five output signal waveforms emanating from the various elements noted below have been illustrated in FIG. 2. Denoted A through D, inclusive, it should be reiterated at this point that these waveforms are coordinated in time, but not necessarily in amplitude. These waveforms respectively represent the output signals from noise generator 11, ramp generator 16, VCO 17, and transistor shunt gate 15.

Noise generator 11 generates a "white noise" output signal A having a "uniform" spectral noise density. In other words, this means that the ratio of the noise output from noise generator 11 within a specific frequency interval to the frequency interval itself is a constant. As shall become more evident hereinafter, it is of no moment to the present invention precisely what this ratio happens to be, it is significant only that it remains constant.

Spectrum modulator 12 receives white noise signal A from noise generator 11 and modulates its spectral noise density in a manner similar to the brain wave patterns associated with relaxed and meditative states. More particularly, spectrum modulator 12 modulates white noise signal A with a variable frequency in the range of frequencies of Alpha brain wave patterns. It has been found to be most effective in inducing a relaxed and meditative state in a subject to begin modulating white noise signal A at a frequency slightly greater than the frequency associated with the Alpha brain wave pattern occurring when the subject is most active, and gradually over a period (T) of minutes reducing the modulation frequency to a frequency slightly less than the frequency associated with the Alpha brain wave pattern occurring when the subject is least active. Upon reaching this lowest modulation frequency, modulation of white noise signal A is terminated, permitting the subject's natural brain wave patterns to become dominant.

A typical operating cycle would begin by the closing of switch 26, resetting ramp generator output signal B to its "zero" voltage $-V$ volts, and forcing VCO output signal C to its highest frequency of 14 Hz. VCO output signal C is mixed with ramp generator output signal B and received by the base of switching transistor 18, causing switching transistor 18 to alternate at the instantaneous frequency of VCO 17 (then 14 Hz) between saturation and cutoff operational states. Diode 19 sets the maximum base-emitter voltage for switching transistor 18.

When operating in a saturated state, switching transistor 18 shunts to ground the higher frequency components of white noise signal A. When operating in a cutoff state, switching transistor 18 permits the full frequency spectrum of white noise signal A to be received by output amplifier 13. The resultant output from spectrum modulator 12 is output signal D shown in FIG. 2.

As time proceeds, the voltage of ramp generator output signal B increases, proportionally decreasing the frequency of VCO output signal C and the modulation frequency of white noise signal A. When the maximum possible positive voltage ($+V$) of ramp generator output signal B is reached, the frequency of VCO output signal C remains at a constant 5 Hz, and switching transistor 18 remains in a saturated state, causing all modulation of white noise signal A to terminate, leaving only the low frequency components of white noise signal A to be received by output amplifier 13.

Output amplifier 13 receives transistor shunt gate 15 output signal D and amplifies it to a level compatible with acoustical transducer 14, which converts the signal to an audio format suitable for direct listening by the subject. Output amplifier 13 only need be furnished where further amplification is required.

Several modifications to the depicted embodiment may be noted. Perhaps most significant is the fact that other spectrum modulation patterns could be employed herein, although the illustrated continuously decreasing spectral density modulation is highly advantageous in inducing a relaxed and meditative condition in a subject. For example, rather than ramp generator 16 generating a continuously increasing voltage signal, continuously decreasing the frequency of VCO 17, it would be possible to provide periods of constant voltage output alternated with periods of changing voltage output, resulting in differing patterns of spectral modulation. An essentially unlimited number of possible combinations may be effected by simple adjustment of the generator 16 output signal waveform.

It should also be appreciated that the particular transistor shunt gate 15 shown herewith is merely exemplary of numerous equally suitable circuits for switching the noise generator output signal A. Transistor shunt gate 15 permits modulation of the higher frequencies contained in the source signal at rates which corrolates to natural Alpha brain wave pattern frequencies and, in this manner modifies the spectral noise density of the source signal.

Inasmuch as the present invention is subject to many variations, modifications and changes in detail, a number of which have been expressly stated herein, it is intended that all matter described throughout this entire specification or shown in the accompanying drawings be interpreted as illustrative and not in a limiting sense. It should thus be evident that a device constructed according to the concept of the present invention, and equivalent thereto, will accomplish the objects of the present invention and otherwise substantially improve the art of the induction of specific brain wave patterns in a subject.

I claim:

1. A device for the induction of brain wave patterns associated with relaxed and meditative states in a subject comprising:
   means for generating a white noise signal having a uniform spectral noise density;
   means for receiving said white noise signal and modulating its said spectral noise density in a manner similar to the brain wave patterns associated with relaxed and meditative states; and
   means receiving said modulated noise signal for coupling said modulated signal to the subject.

2. A device, as set forth in claim 1, wherein the brain wave patterns associated with relaxed and meditative states occur in a range of freqencies, said means for modulating the spectral noise density including means for modulating said white noise signal beginning at a frequency greater than that of the brain wave patterns.

3. A device, as set forth in claim 2, wherein said means for modulating the spectral noise density further includes means for gradually reducing the frequency at which said spectral noise density is modulated.

4. A device, as set forth in claim 3, wherein said means for modulating the spectral noise density further includes means for terminating all modulation of said white noise signal upon reaching its lowest frequency of modulation.

5. A device, as set forth in claim 3 or 4, wherein said means for modulating the spectral noise density further includes means for reaching a steady state frequency of modulation at a frequency slightly lower than the lowest said brain wave pattern frequency.

6. A device, as set forth in claim 5, wherein said means for modulating said spectral noise density includes switching means for receiving said white noise signal, providing said modulated noise signal, and periodically shunting to ground the high frequency components of said white noise signal.

7. A device, as set forth in claim 6, wherein said means for modulating said spectral noise density further includes oscillator means for controlling the instantaneous frequency at which said switching means periodically shunts to ground said high frequency components of said white noise signal and generator means for controlling the instantaneous frequency of said oscillator means.

8. A device, as set forth in claim 7, wherein said generator means generates an output signal having a variable voltage, which signal is received by said oscillator means and causes said oscillator means to generate a modulation signal having a frequency of from approximately 14 to 15 Hz.

9. A device, as set forth in claim 8, wherein said output signal from said generator means begins operation at its negative most voltage amplitude and continuously gradually increases to a steady-state value at its positive most voltage amplitude, said oscillator means beginning operation at approximately 14 Hz and continuously gradually increasing to a steady-state value at approximately 5 Hz, whereby said switching means modulates the high frequency components of said white noise signal at the instantaneous frequency of said oscillator means.

10. A device, as set forth in claim 9, wherein said means for coupling said modulated signal to the subject is a headphone transducer for converting said modulated signal to an audio signal and having pneumatic tubes adopted to carry said audio signal to the subject in a non-intrusive manner while minimizing extraneous acoustical background distractions.

11. A device, as set forth in claim 10, wherein said switching means includes a switching transistor furnishing said modulated signal, and further including an output amplifier receiving and amplifying said modulated signal, said headphone transducer receiving said amplified modulated signal from said output amplifier.

* * * * *